United States Patent [19]
Krebs

[11] Patent Number: 6,146,407
[45] Date of Patent: Nov. 14, 2000

[54] SUTURE ANCHOR INSTALLATION DEVICES AND METHODS

[75] Inventor: Steven L. Krebs, Temple, Tex.

[73] Assignee: Bio Innovation, Ltd., Fort Wayne, Ind.

[21] Appl. No.: 09/151,954

[22] Filed: Sep. 11, 1998

[51] Int. Cl.$^7$ ................................................ A61B 17/04
[52] U.S. Cl. ............................ 606/232; 606/73; 606/104
[58] Field of Search .......................... 606/72, 75, 104, 606/232

[56] References Cited

U.S. PATENT DOCUMENTS

| | | | |
|---|---|---|---|
| 4,741,330 | 5/1988 | Hayhurst | 606/232 |
| 5,156,616 | 10/1992 | Meadows et al. | 606/232 |
| 5,411,523 | 5/1995 | Goble | 606/232 |
| 5,573,548 | 11/1996 | Nazre et al. | 606/232 |
| 5,690,676 | 11/1997 | DiPoto et al. | 606/232 |
| 5,733,307 | 3/1998 | Dinsdale | 606/232 |
| 5,814,051 | 9/1998 | Wenstrom, Jr. | 606/104 |
| 5,904,704 | 5/1999 | Goble et al. | 606/232 |
| 5,993,477 | 11/1999 | Vaitekunas et al. | 606/232 |

*Primary Examiner*—Gary Jackson
*Attorney, Agent, or Firm*—Taylor & Aust, P.C.

[57] ABSTRACT

A suture anchor is described having a central shaft and at least one outwardly extending longitudinal rib. The ribs may have bone engaging elements such as threads or barbs on their outer surfaces. A bone boring tool having more than one set of sharpened cutting edges is described which creates a non-circular hole in bone approximating the anchor cross section geometry. The suture anchor is inserted into the shaped hole in bone and is rotated about its axis by the driver to engage the ribs with the bone.

3 Claims, 13 Drawing Sheets

SUTURE ANCHOR INSTALLATION DEVICES AND METHODS

FIELD OF THE INVENTION

This invention relates to soft tissue anchoring devices for securing ligament or tendon to bone. This invention also relates to an installation tool and method for inserting the anchoring device into bone.

DESCRIPTION OF THE PRIOR ART

There are a variety of methods for soft tissue attachment to bone in the prior art. The oldest technique requires holes to be made through bone. The suture is passed through the holes and is used to tie the soft tissue to the bone. This method is still used today in older osteoarthritic patients, but it is considered difficult and time consuming with increased trauma to the patient.

Other methods involve using soft tissue anchoring devices. There are many types of anchoring devices disclosed in the prior art. Several approaches to stapling or tacking soft tissue to bone have been used. An example of a staple device is disclosed in U.S. Pat. No. 4,873,637. This teaches a staple device having two or more leg portions and a body disposed between the legs. An example of a tacking device is taught in U.S. Pat. No. 4,873,976. It teaches a nail with multiple barbs and a tissue retaining head. Drawbacks of these types of devices are that they are relatively large and require anchor sites of greater bone stock which limits their application. They can also can break or split bone on their deployment.

Other soft tissue anchoring devices disclosed in the prior art describe suture anchors. These devices are composed of an anchor and a surgical suture. The anchor is installed in the bone. Then the suture is passed through the soft tissue and tied to the bone surface. Examples of these devices are taught in U.S. Pat. No. 5,013,316 which describes a metallic threaded suture anchor and U.S. Pat. No. 5,046,513 which describes a metallic anchor with elastic barbs. Drawbacks of these devices include anchor loosening and migration, patient sensitivity to nickel, corrosion of metals and interference with imaging techniques such as MRI.

U.S. Pat. No. 5,690,678 teaches the use of a slot and subsurface channel machined into bone. Suture is anchored to the bone with knots or beads. Orientation of the slot is critical in this system. If mechanical forces move the knot or bead to the introduction hole, the suture can become dislodged from the bone. U.S. Pat. No. 5,569,303 also discloses anchors deployed in a slot machined in bone. The anchor is inserted with its long axis parallel with the bone surface and rotated about the short axis of the anchor. A slot machined in bone as described in both of the above patents, creates a large defect in bone in comparison to devices installed perpendicular to the bone surface. The larger the defect, the greater the risk to the structural integrity of the surrounding bone. This limits the application of this device to good quality bone only. Also, a machined slot can allow for increased movement of the sutures along the machined bone surfaces. This can abrade and weaken the suture which can lead to premature failure.

Suture anchors can also be fabricated of bioabsorbable materials which are absorbed over time in the body and replaced by bone. This may reduce the possibility of joint damage due to anchor loosening and migration. Also, bioabsorbable polymers do not interfere with imaging techniques such as MRI. Examples of these devices are taught in U.S. Pat. No. 5,573,548 which teaches a bioabsorbable threaded suture anchor and U.S. Pat. No. 5,584,836 which describes a threaded, cannulated absorbable suture anchor. These devices offer advantages because they are made of absorbable polymer. This feature also means that they lack the hardness to be self tapping as in metal anchors. Consequently bioabsorbable suture anchors with screw threads require increased site preparation. Drilling and tapping threads into bone must be completed prior to installation of the anchor.

The primary object of this invention is to provide an improved soft tissue anchor which is mechanically stable, easy to manufacture, use and install. Another object of the present invention is to provide an improved bone boring tool wherein the tool is used to create a non-circular shaped hole in bone approximating the cross section of the anchoring device. Still another object of this invention is to provide a novel method for deploying the soft tissue anchor in bone.

SUMMARY OF THE INVENTION

In accordance with the objects above, the present invention is a suture anchor assembly, bone boring tool and method of insertion for attachment of soft tissue to bone. The apparatus comprises a suture anchor, suture, bone boring tool and insertion tool.

The suture anchor described herein is used in the following way. The suture anchor has an elongated body. At least one rib extends outward from, and runs longitudinally along all or a portion of the body. The ribs may include bone engaging elements such as threads or barbs. The anchor has a through hole proximate to the midpoint for the smooth passage of suture. The proximal end has a geometry which mates with the drive tip of the insertion tool. The preferred embodiment is the anchor made of a bioabsorbable polymer.

The bone boring tool creates a shaved hole in bone. This is a hole which closely approximates the anchor cross section, including the longitudinal ribs. The tool first bores a circular hole in the bone. When the lateral cutters contact the bone surface, the tool is used as a punch to cut the slots for the anchor ribs. The boring tool may also be equipped with an adjustable depth stop to prevent cutting too deeply into the bone.

The suture is threaded through the suture anchor and assembled to the insertion tool by fitting the proximal anchor end into the drive tip of the insertion device. The anchor is placed into the shaped hole in bone to the correct depth. The anchor is rotated about its long axis to lock it into the bone. The insertion tool is removed and the free suture ends are used to tie the soft tissue to the bone surface.

The present invention solves many of the problems of the prior art by providing a body absorbable suture anchor. A bioabsorbable anchor avoids most of the concerns associated with the metallic anchors such as imaging problems, loosening and migration and metals sensitivity.

The present invention also provides a novel means of insertion and locking into bone. This addresses the concerns associated with drilling and tapping in bone for polymeric threaded anchors. Tapping in bone requires a constant pressure and axial orientation of the tap to prevent overcutting or stripping of threads cut in bone. Whereas, the bore/punch procedure requires fewer steps and less precision. The center cutter bores a circular hole in the bone and the same tool is used to punch radial slots, creating a non-circular hole approximating the anchor cross section geometry. This avoids any concerns about cross-threading anchors or tapping holes in bone. Unlike the devices using slots cut into bone, the device of the present invention is introduced perpendicular to the surface of the bone. This requires a much smaller hole to be cut into the bone which helps to maintain the bone's structural integrity. A smaller hole is particularly advantageous when the anchor is placed into bone of medium or poor quality. The device of the present invention is rotated about its long axis. This requires less force than rotation about the short axis of the device. Over stressing the device during the rotation can weaken the device which can lead to premature device failure.

The foregoing and other features and advantages of the present invention will become more apparent from the following description and accompanying drawings.

DESCRIPTION OF THE DRAWINGS

Corresponding reference characters indicate corresponding parts throughout the several views of the drawing.

DETAILED DESCRIPTION OF THE INVENTION

The following descriptions of the preferred embodiment are not intended to be exhaustive or to limit the invention to the precise forms disclosed. Rather they are chosen to explain the invention so that one skilled in the art might utilize their teachings.

Figure 1:
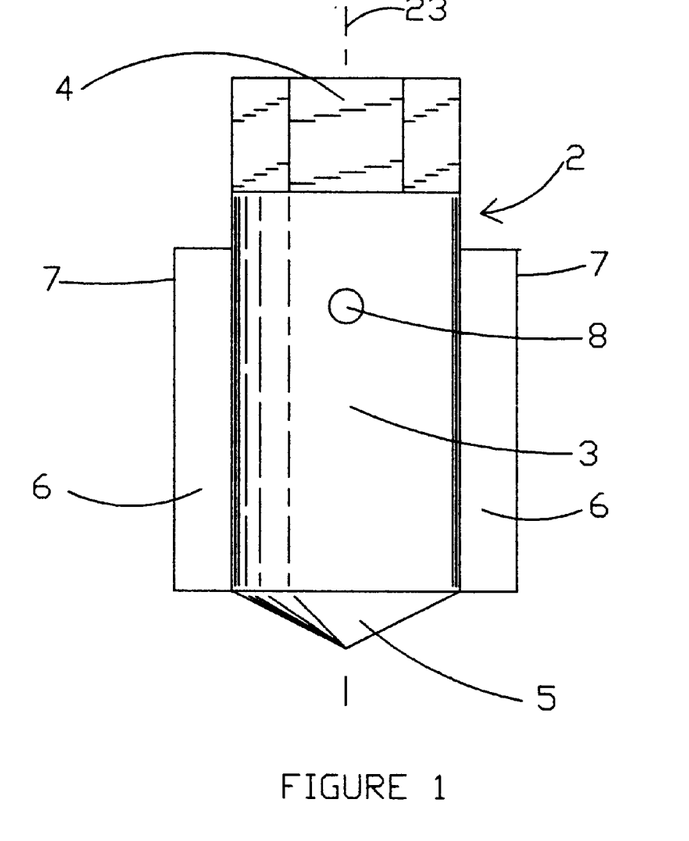
FIG. 1 is a side view of a soft tissue anchor according to the present invention.
Figure 2:
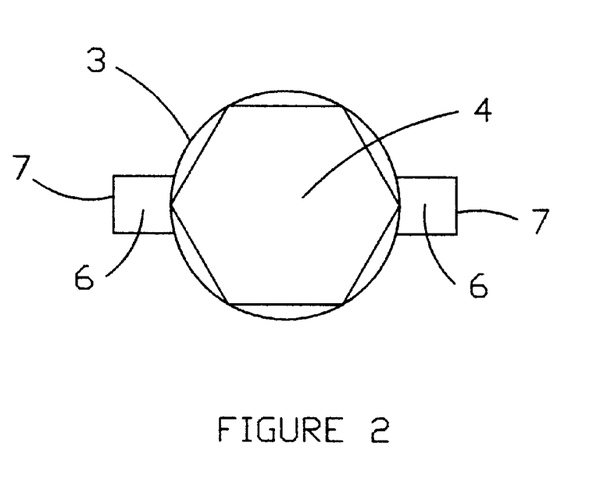
FIG. 2 is an end view of a soft tissue anchor according to the present invention.
Figure 8:
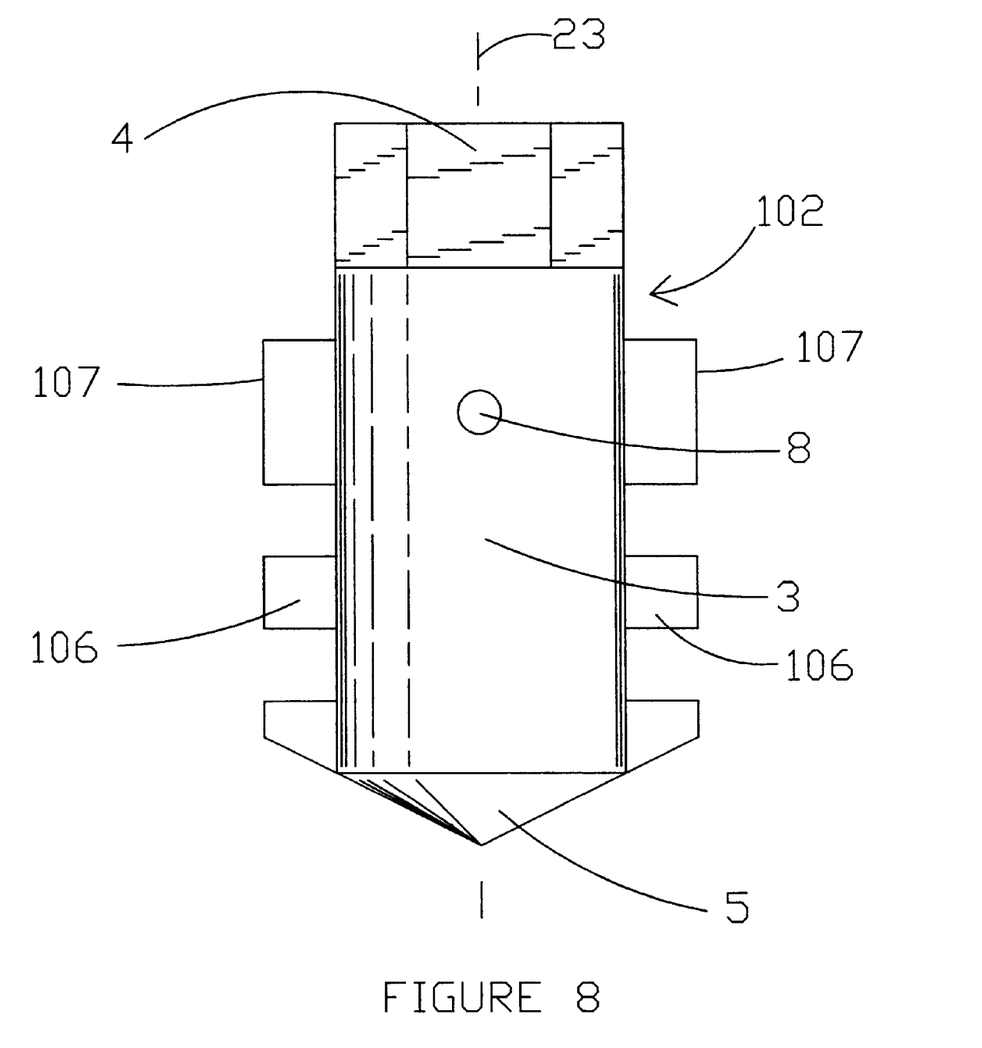
FIG. 8 is a side view of a soft tissue anchor having discontinuous anchor ribs of varied lengths.
Figure 9:
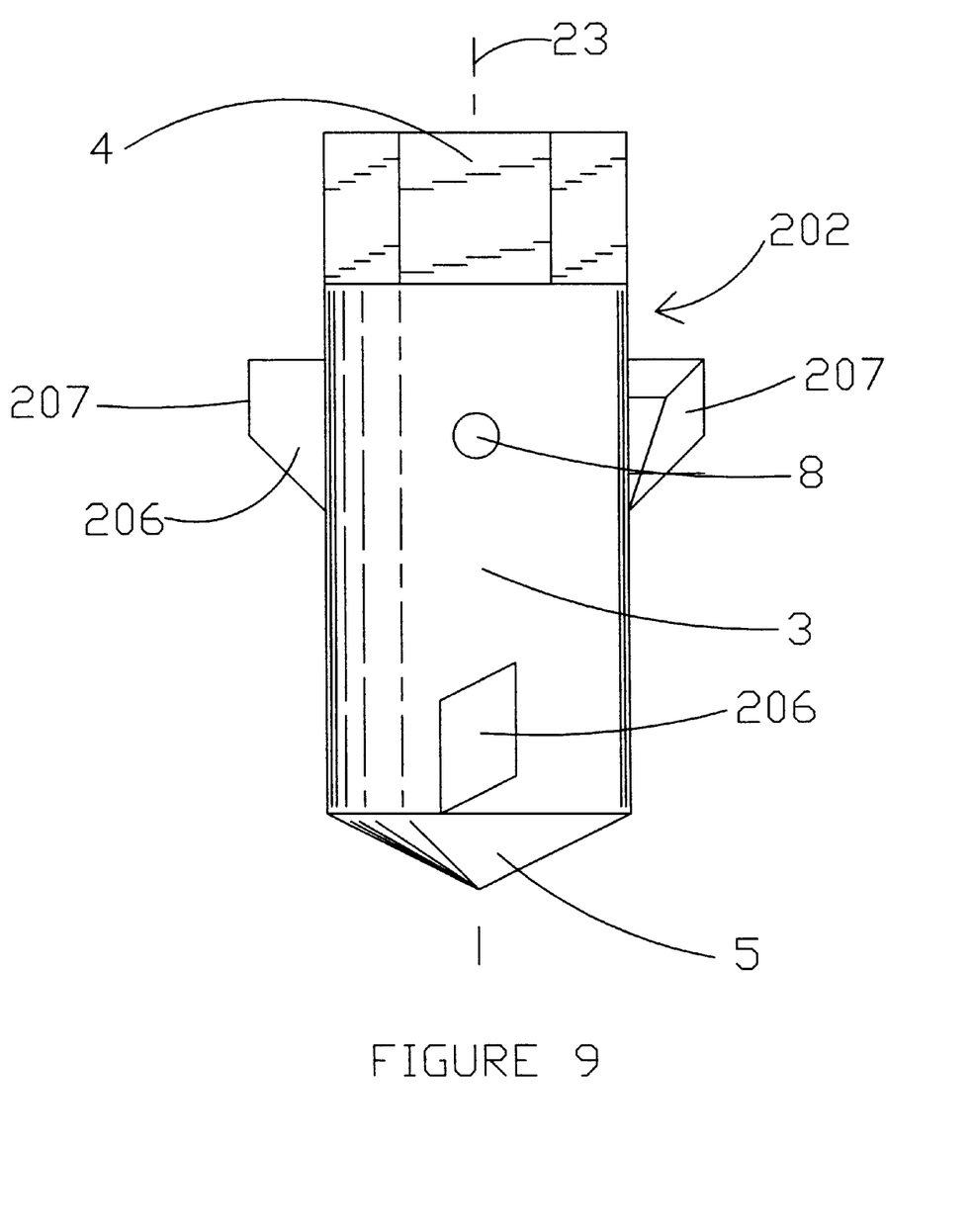
FIG. 9 is a side view of a soft tissue anchor having discontinuous anchor ribs in varied positions and having irregular surfaces.
Figure 10:
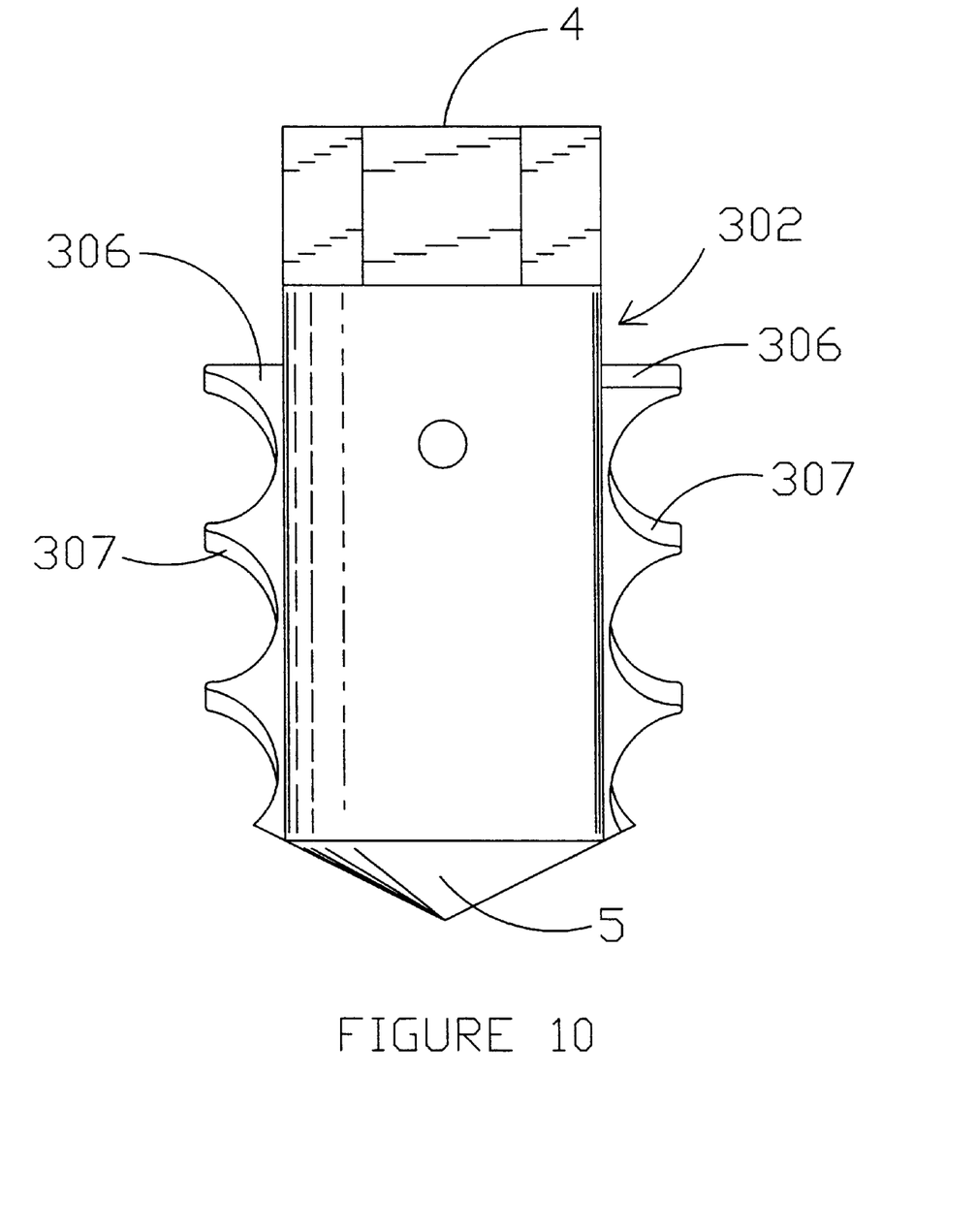
FIG. 10 is a side view of a soft tissue anchor having continuous anchor ribs with threads.

FIGS. 1 and 2 illustrate one embodiment of the invention. The suture anchor 2 is comprised of an elongated body 3 having a proximal 4 and distal 5 end. The device has at least one longitudinal rib 6. The ribs 6 are attached to the anchor body 3 and may extend the full length of the anchor body 3 or only a portion thereof. The ribs 6 may be continuous or discontinuous and may be of varied lengths and positions about the anchor body 3. FIG. 8 illustrates a modified embodiment with an anchor 102 having discontinuous ribs 106 with the rib segments having varied axial lengths. FIG. 9 illustrates yet another embodiment of an anchor 202 having discontinuous ribs 206 located in varied positions and having irregular or skewed surfaces. The ribs 6 may contain bone engaging features 7, 107 or 207 on their lateral faces such as buttressed or cutting threads, etc. FIG. 10 illustrates a still further embodiment as the anchor 302 having continuous ribs 306 with buttressed threads 307 on the lateral faces. The cross section of the anchor body 3 may be of a varied geometry and the cross sections may vary over the length of the body 3. The through hole 8 is placed proximate to the midpoint of the anchor body 3. The through hole 8 is large enough to allow the smooth passage of suture. The proximal end 4 of the suture anchor 2 has a geometry which approximates and is adapted to mate with the drive tip of the insertion tool shown in FIGS. 5 and 6 and is conducive to rotating the anchor 2 about its longitudinal axis 23. The transverse geometric cross sections of the suture anchor 2 conform to the geometry cut by the bone boring tool of FIGS. 3 and 4.

The material of construction for this preferred embodiment of the suture anchor 2 is a biocompatible body absorbable polymer. Examples of these include homopolymers or copolymers of lactide, glycolide, trimethylene carbonate, caprolactone, p-dioxanone and blends or other combinations thereof. The preferred material is poly (lactic acid). The preferred method of manufacture of the anchor device is injection molding. It is fast, highly reproducible and delivers consistent quality.

Figures 3, 4:
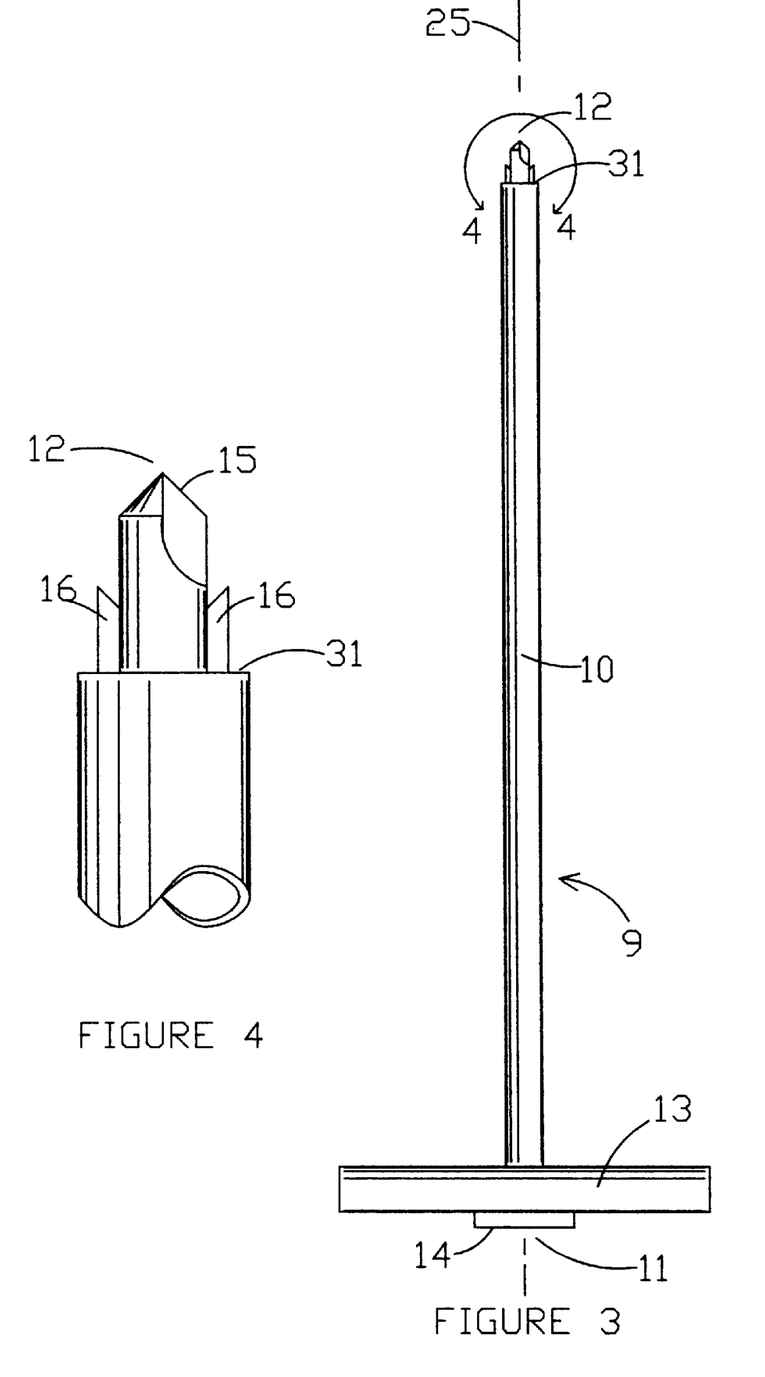
FIG. 3 a side view of the bone boring tool according to the present invention.
FIG. 4 is an expanded view of the boring tool cutters according to the present invention.

FIGS. 3 and 4 illustrate one embodiment of the bone boring tool 9. The bone boring tool 9 is comprised of a central shaft 10 having a proximal 11 and distal 12 end. The proximal end 11 has a handle 13 for rotation of the instrument about the its longitudinal axis 25. The proximal end 11 also has a flattened area for impacting the tool to punch the radial slots into the bone. The distal end 12 has two sets of sharp edges for cutting bone. The distal-most cutters 15 are used to bore, by tool rotation, the initial circular hole into the bone large enough to accept the suture anchor body 3. The radial cutters 16 are set a given distance proximally from the distal-most cutters 15. The radial cutters 16 will punch, by axial tool motion, the slots 30 into the bone at the required locations to accept the anchor ribs 6. The distal end 31 of the bone boring tool 9 functions as a depth gauge limiting the penetration depth of the radial cutters 16.

Figure 11:
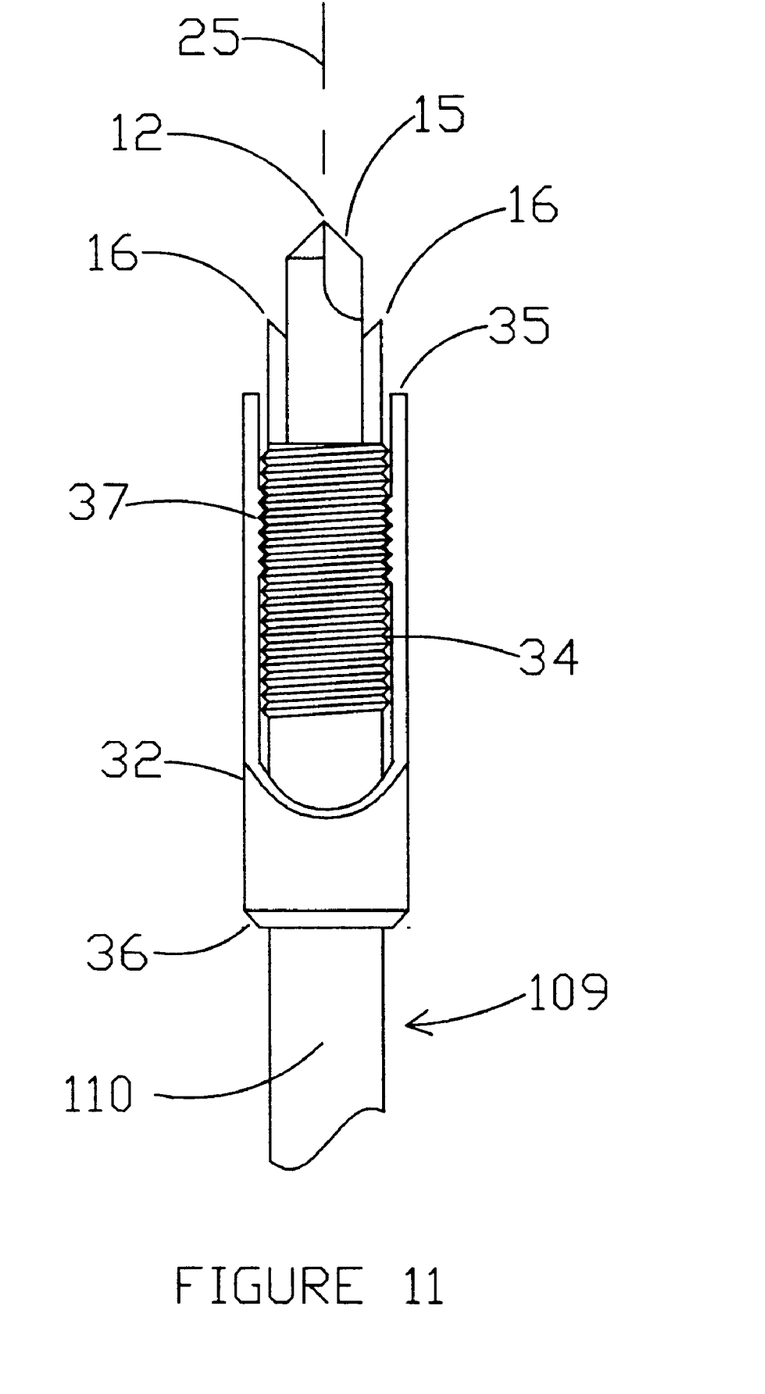
FIG. 11 is a cut away side view of the tip portion of a bone boring tool similar to FIGS. 3 and 4, but illustrating one variation thereon.

FIG. 11 illustrates an embodiment of the bone boring tool 109 having an adjustable depth feature. The bone boring tool of FIG. 3 is modified by the addition of helical threads 34 about the shaft 110. An outer sleeve 32 having distal 35 and proximal 36 ends, and interior helical threads 37 is threadedly received on and rotatable about the central shaft 110. As sleeve 32 is rotated relative to the central shaft 109, it moves axially therealong changing the axial separation between the distal end 35 and the cutters 15 and 16. End 35 assumes the function of end 31 of FIGS. 3 and 4 providing an adjustable stop limiting the depth of penetration of the cutters into bone.

Figure 12:
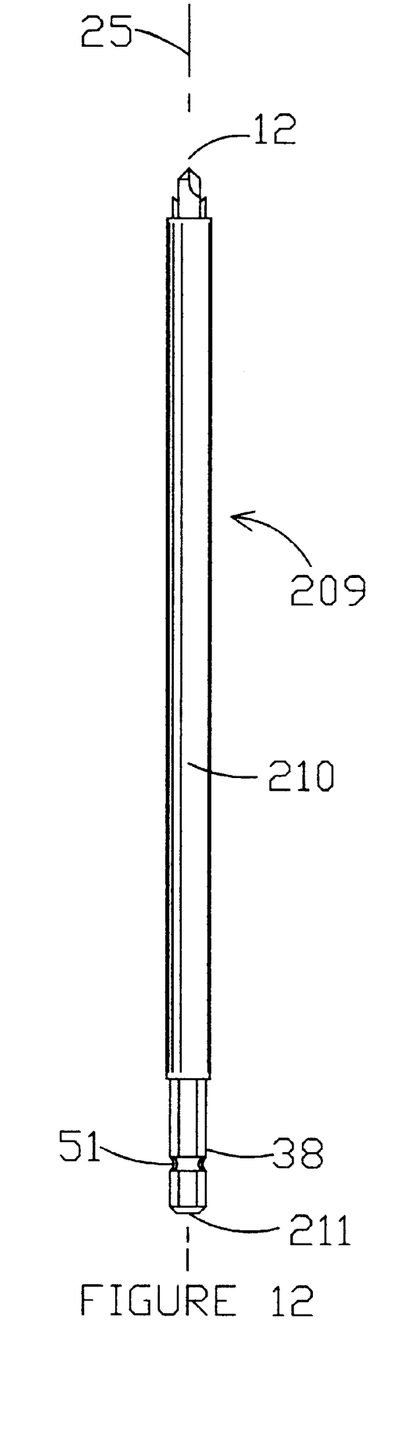
FIGS. 12 and 13 are side views of a bone boring tool and handle respectively similar to FIG. 3, but illustrating a quick connect feature.
Figure 13:
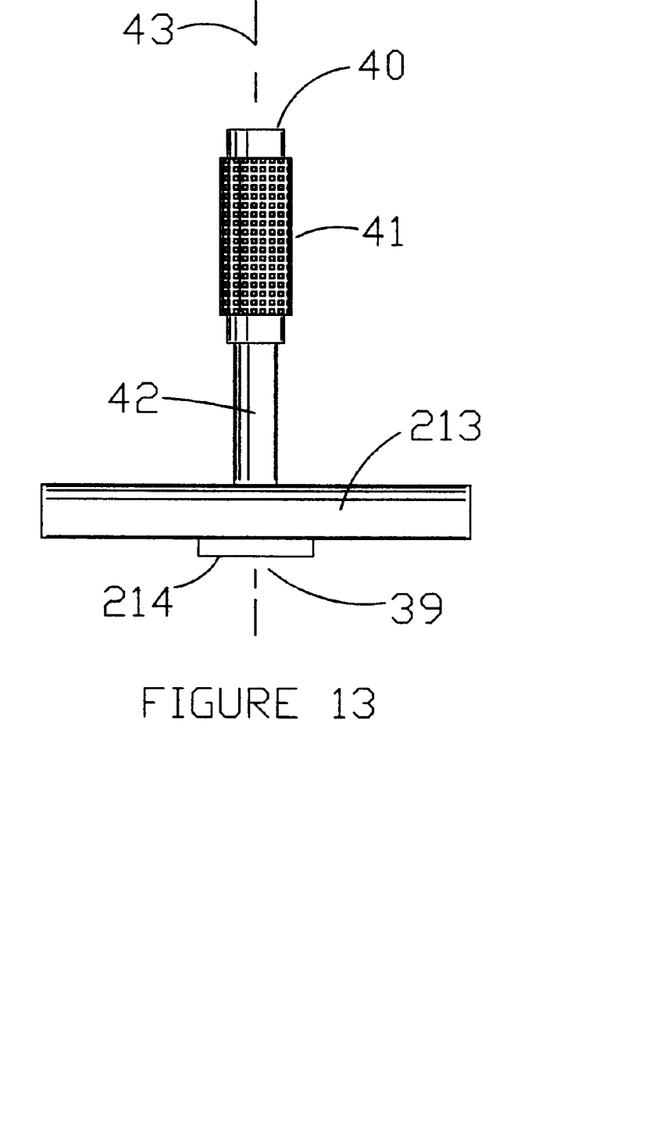

A quick connect feature will allow the bone boring tool to be connected quickly to a power drill for boring the initial circular hole 29 and then be interchanged to use the handle for punching the radial slots 30 into bone. In FIG. 12, the bone boring tool 209 has a standard male quick connect coupling 38 on the proximal end 211 of the tool central shaft 210, and the handle 213 of FIG. 13 is coupled to a central shaft 42 having a standard female quick connect coupling 41 near the distal end 40 thereof. For example, the male quick connect coupling 38 may comprise a hexagonal shaft with an undercut region or groove 51 while the female quick connect coupling 41 may include an outer sleeve surrounding and engaging a collet alone a common taper with the sleeve spring loaded to close the collet about the shank and engage the groove 51. Alternatively, one or more radially biased detent balls within the coupling 41 may function to engage the groove 51 thereby joining the tool and handle. The handle proximal end 39 includes a flattened area 214 for impacting the tool to punch the radial slots 30 into the bone. Handle 213 may, of course, be used to rotate the handle portion about axis 43, which is coaxial with axis 25 when the handle and tool are joined, to bore the hole as with the embodiment of FIG. 3.

Figures 5, 6:
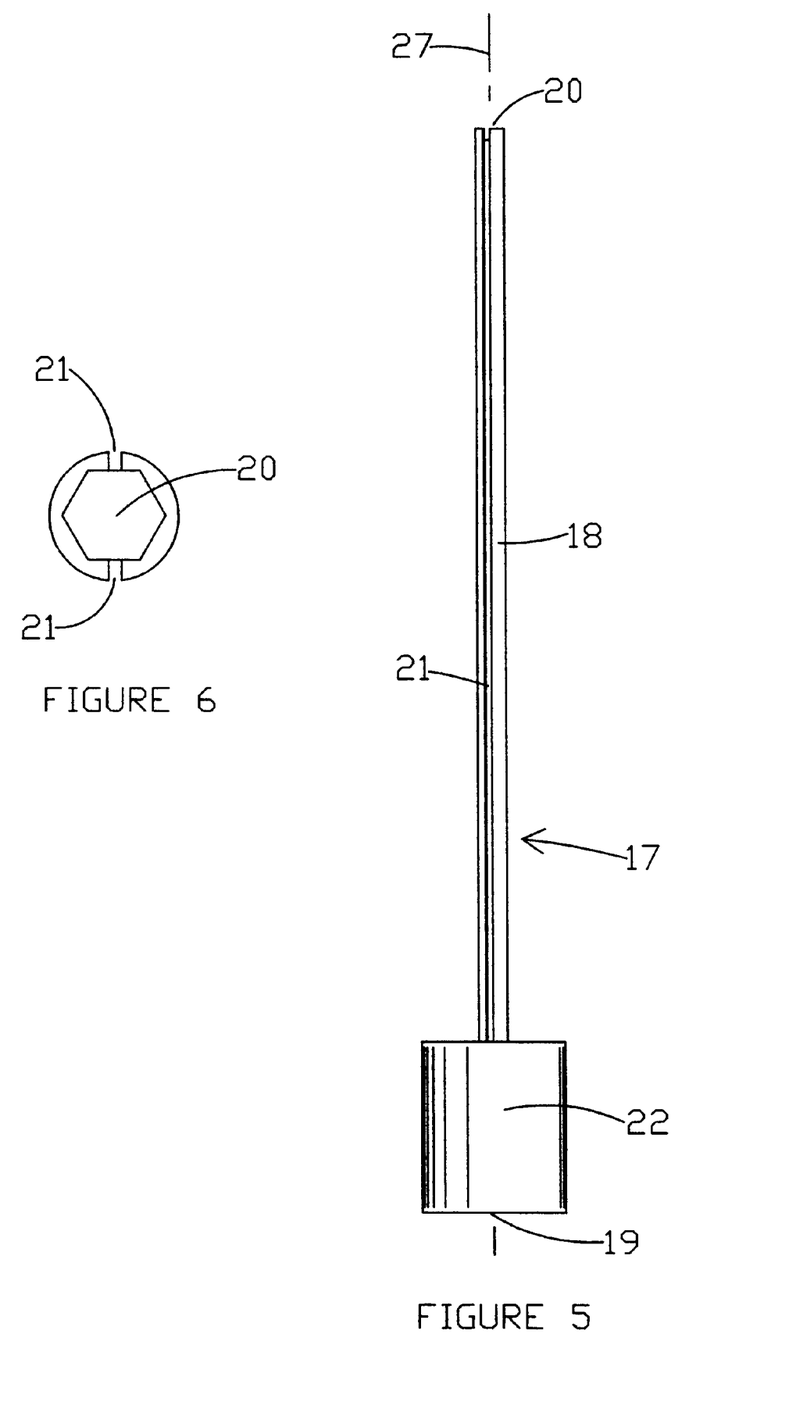
FIG. 5 is a side view of the insertion tool.
FIG. 6 is an enlarged view of the distal tip of the insertion tool.

FIGS. 5 and 6 illustrate the insertion tool 17. The insertion tool 17 is comprised of a central shaft 18 having a proximal 19 and distal 20 end. The central shaft 18 has a longitudinal slot 21 to accommodate the suture elements. The distal end 20 has a geometry, a hexagonal concavity as illustrated, which approximates and mates with the geometry of the proximal end 4 of the suture anchor 2 such that the insertion tool 17 is capable of driving the suture anchor 2 about its axis 23 during installation. The proximal end 19 has a handle 22 for rotating the insertion tool 17 about axis 27 and for storing the free ends of the suture until the anchor 2 is deployed in bone.

The method used to install the suture anchor 2 into bone is as follows:

The suture is placed through the anchor through-hole 8. The suture anchor 2 is assembled to the insertion tool 17 by fitting the proximal end 4 of the suture anchor 2 into the distal end 20 of the insertion tool 17. The lengths of the suture are placed into the longitudinal slot 21 of the insertion tool 17, and the free ends of the suture are stored in the handle 22. The anchor 2, suture and installation tool 17 assembly is sterilized prior to use.

Figure 14:
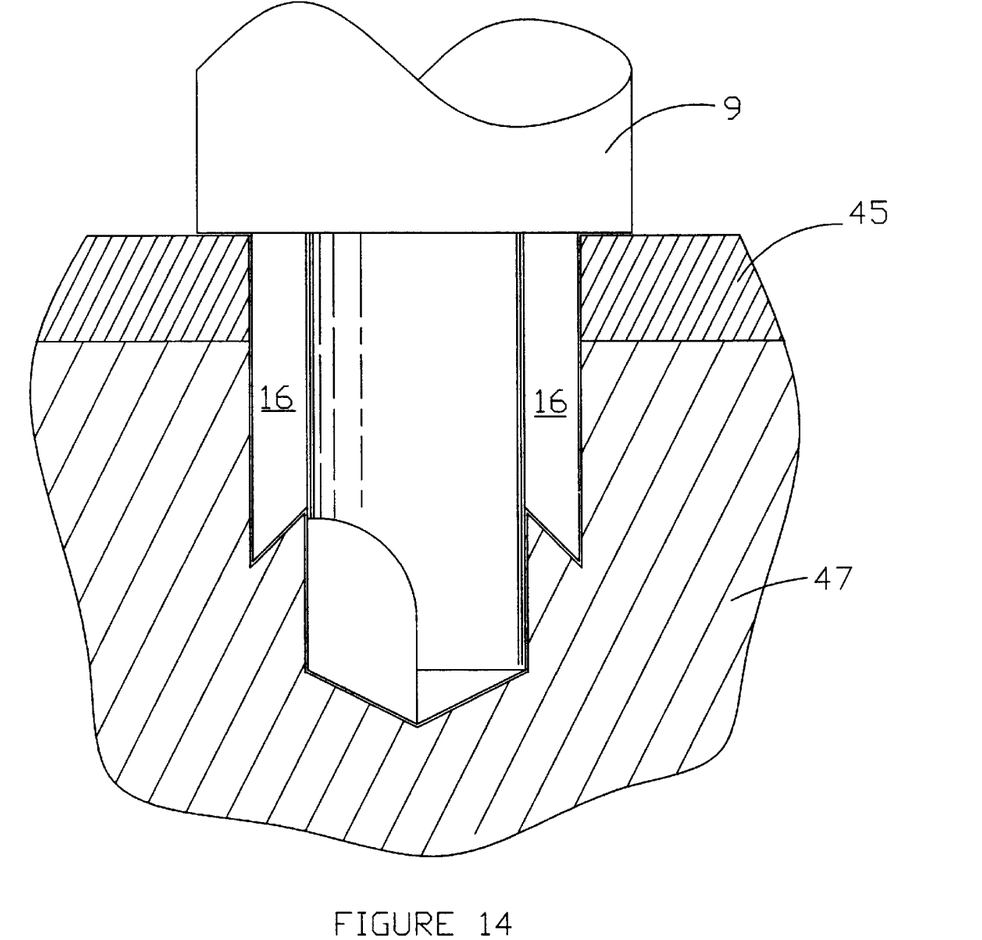
FIG. 14 is a cut away side view illustrating the bone boring tool cutting a formed hole in bone.

The bone boring tool 9 is used by placing the distal-most cutters 15 at the desired location on the bone surface. The bone boring tool 9 is rotated about its longitudinal axis 25 with some axial pressure until a circular hole 29 is cut into the bone. This hole is sized to fit the anchor body 3. When the boring tool 9 has cut to a fixed depth, the radial cutters 16 will begin to contact the surface of the bone. At this time the boring tool 9 is impacted on the flattened proximal area 14 to drive the radial cutters 16 through the cortical region 45 and into the cancellous or inner bone tissue 47. Of course, the transition between the relatively harder outer bone surface 45 and the relatively softer inner region 47 is somewhat gradual and irregular. The straight line of demarcation between the two is idealized. This action punches out the radial slots 30 in the bone which accommodate the anchor ribs 6. FIG. 14 illustrates the boring tool 9 in its final position having formed a hole in the bone. The bone boring tool 9 is then removed from the hole in the bone.

Figure 7:
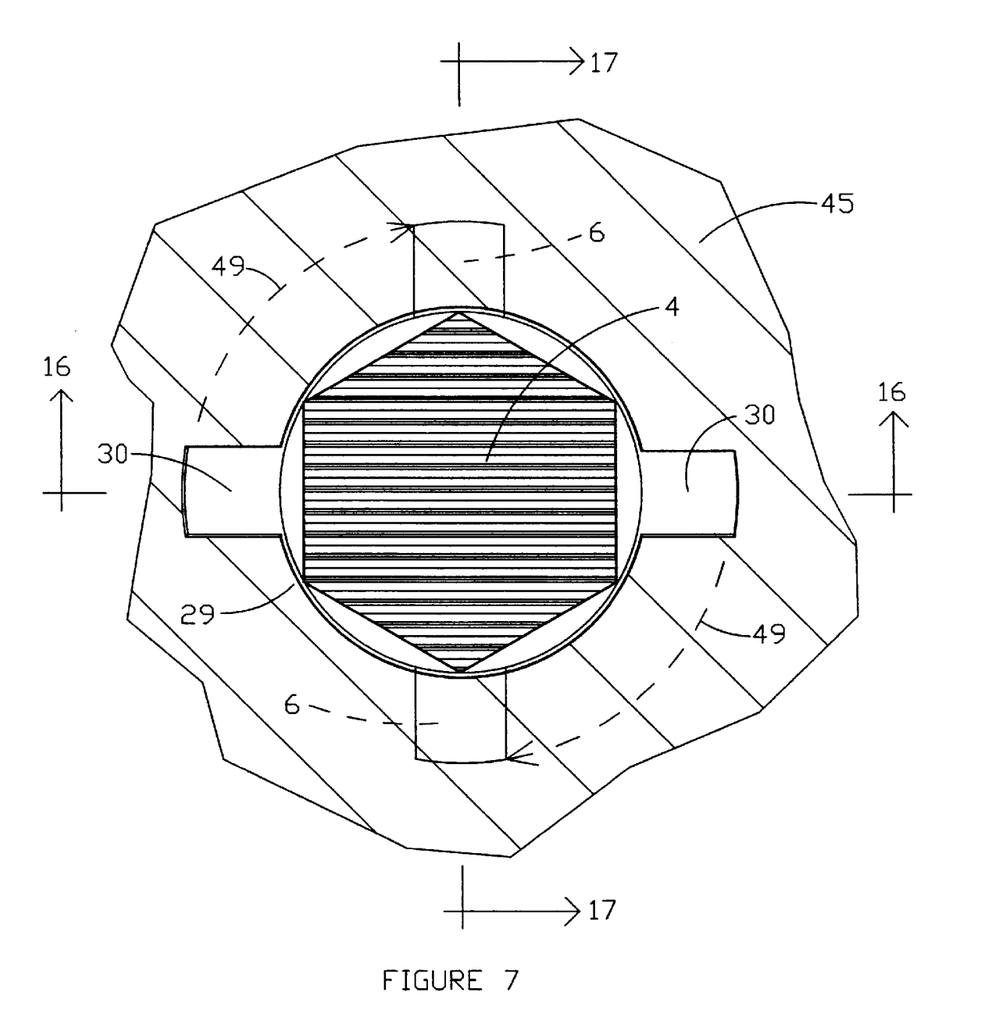
FIG. 7 is a top cross-sectional view along lines 7—7 of FIG. 16 illustrating the anchor deployed in bone.
Figure 15:
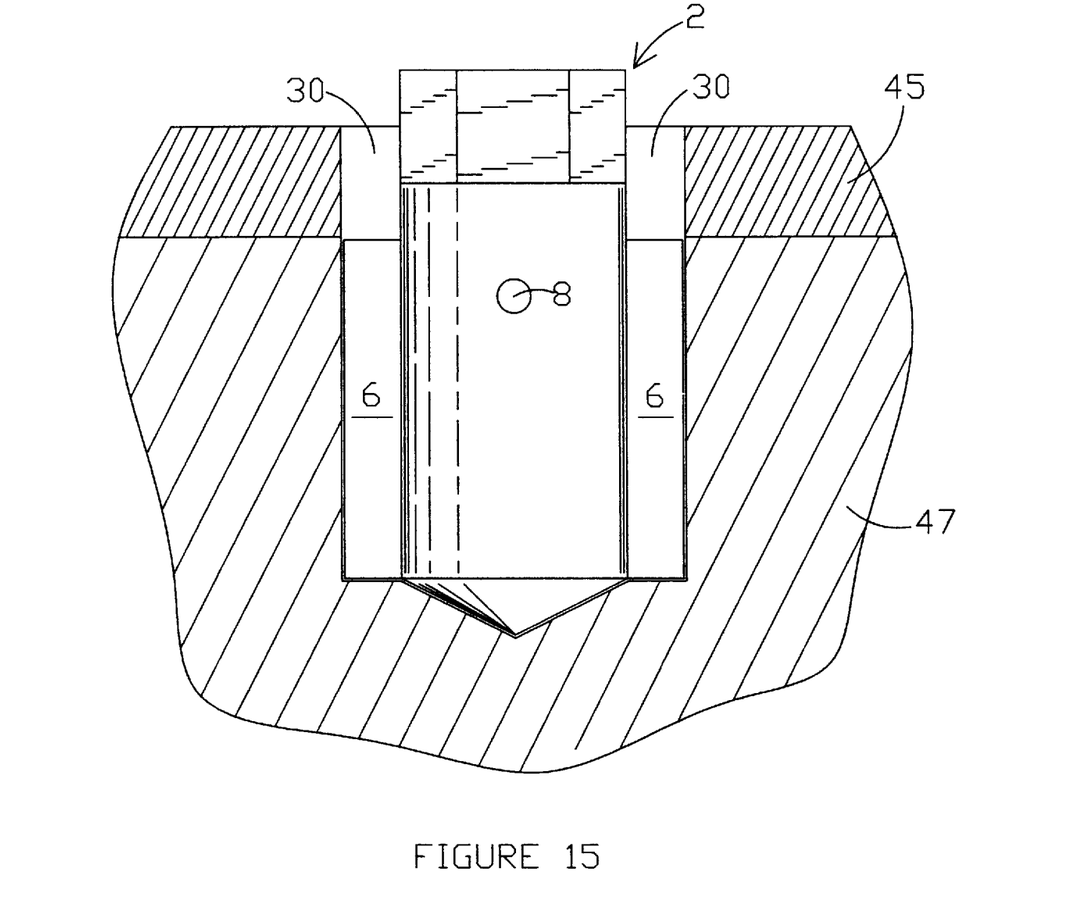
FIG. 15 is a cut away side view of an anchor inserted in a formed hole in bone.
Figure 16:
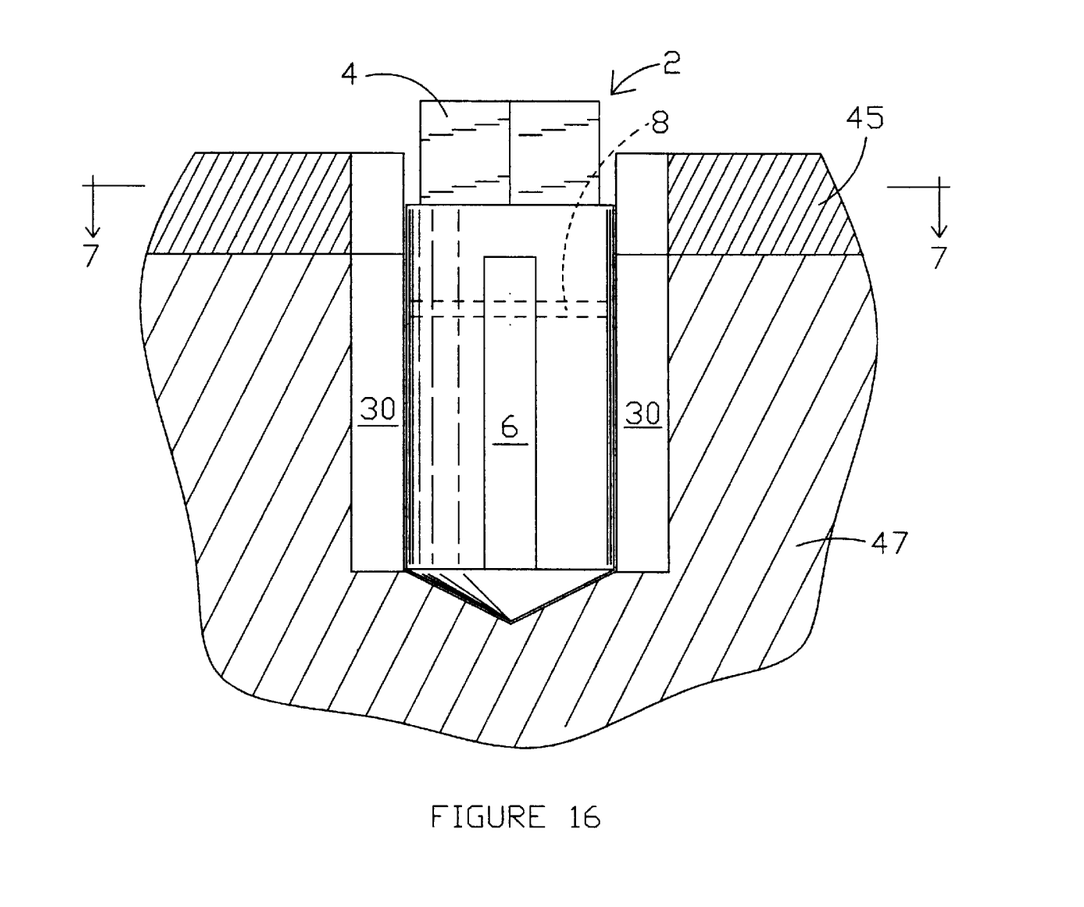
FIG. 16 is a cut away side view generally along lines 16—16 of FIG. 7 showing the anchor of FIG. 15 rotated and locked in bone.
Figure 17:
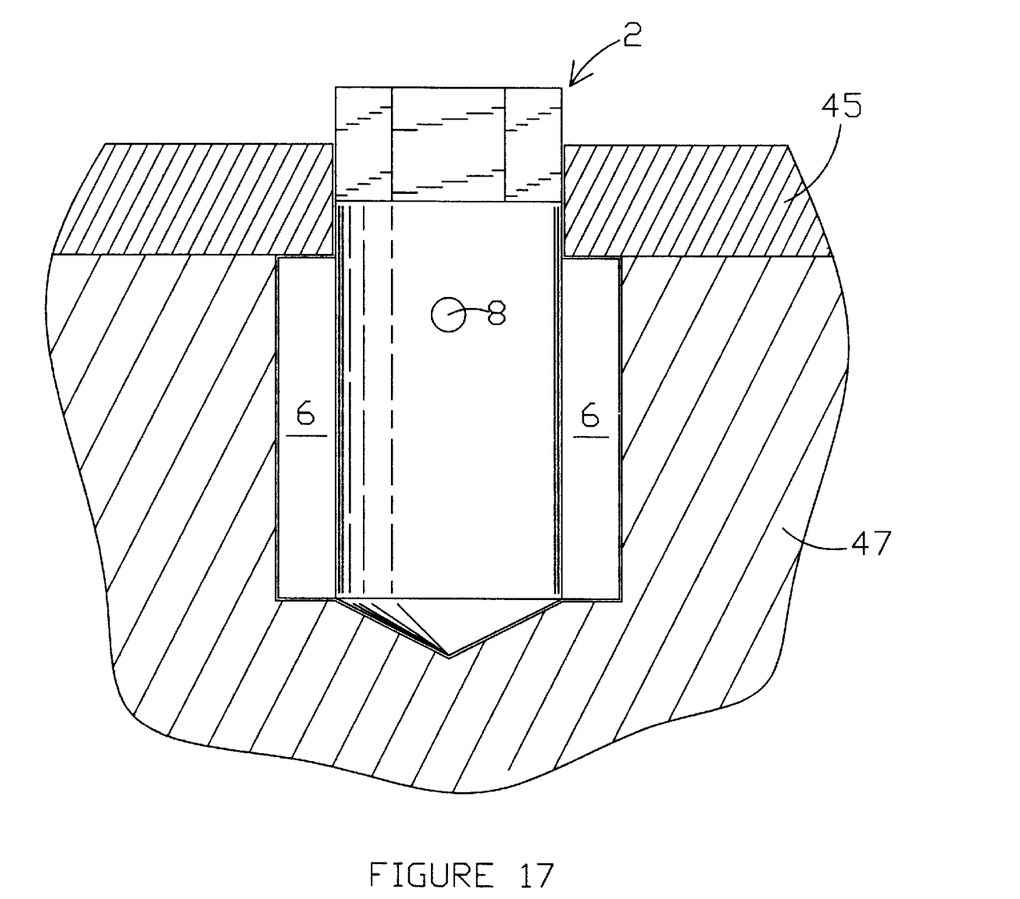
FIG. 17 is a cut away side view generally orthogonal to FIG. 16 and along lines 17—17 of FIG. 7 showing the anchor rotated and locked in bone.

The loaded suture anchor 2 is placed into the shaped hole in the bone using the insertion tool 17. The anchor 2 is inserted into the bone until the proximal surfaces of the ribs 6 are below the cortical bone 45 as shown in FIG. 15. FIG. 16 shows the anchor 2 after being rotated about its longitudinal axis 23 using the proximal handle 22 on the insertion tool 17 to lock the anchor into the bone. FIG. 7 shows the anchor in the shaped hole. The anchor is locked in bone by rotating the anchor as indicated by lines 49 to cut a path through the cancellous bone, locking the anchor below the cortical bone. Thus, the anchor ribs sculpt there own path within a region of softer bone. The insertion tool 17 is withdrawn, which also deploys the free ends of the suture from the proximal handle 22. The suture ends are then used to tie the soft tissue to the anchor and thus to the bone.

From the foregoing, it is now apparent that a novel suture anchor as well as bone preparation and suture placement tools have been disclosed meeting the objects and advantageous features set out hereinbefore as well as others, and that numerous modifications as to the precise shapes, configurations and details may be made by those having ordinary skill in the art without departing from the spirit of the invention or the scope thereof as set out by the claims which follow.

What is claimed is:

1. A suture anchor injection molded of a biocompatible body absorbable polymer comprising a central body having a length and provided with at least one outwardly extending longitudinal anchor rib, the at least one anchor rib being discontinuous over the length of the central body, the central body having a through-hole for receiving a suture, a distal end, and a proximal end adapted to be engaged and rotated by an insertion tool.

2. A suture anchor injection molded of a biocompatible body absorbable polymer, the suture anchor comprising:

a central body provided with at least two outwardly extending longitudinal anchor ribs, the anchor ribs being of varied lengths and positions about the central body, the central body having a through-hole for receiving a suture, a distal end and a proximal end adapted to be engaged and rotated by an insertion tool.

3. A suture anchor injection molded of a biocompatible body absorbable polymer, the suture anchor comprising:

a central body provided with at least one outwardly extending longitudinal anchor rib, the at least one anchor rib extending linearly along the central body, the central body having a through-hole for receiving a suture, a distal end and a proximal end adapted to be engaged and rotated by an insertion tool.

* * * * *

UNITED STATES PATENT AND TRADEMARK OFFICE
CERTIFICATE OF CORRECTION

PATENT NO. : 6,146,407
DATED : November 14, 2000
INVENTOR(S) : Stephen L. Krebs

It is certified that error appears in the above-indentified patent and that said Letters Patent is hereby corrected as shown below:

<u>Column 5</u>
line 9, delete "alone" and substitute --along-- therefor.

Signed and Sealed this

First Day of May, 2001

Attest:

NICHOLAS P. GODICI

Attesting Officer     Acting Director of the United States Patent and Trademark Office